(12) United States Patent
Chen et al.

(10) Patent No.: US 9,339,234 B2
(45) Date of Patent: May 17, 2016

(54) SYSTEM AND METHOD FOR MEASURING PHYSIOLOGICAL PARAMETERS

(75) Inventors: Chieh-Hsing Chen, Changhua County (TW); Chih-Lung Yeh, Changhua County (TW)

(73) Assignee: BIONIME CORPORATION, Dali, Taichung County (TW)

( * ) Notice: Subject to any disclaimer, the term of this patent is extended or adjusted under 35 U.S.C. 154(b) by 358 days.

(21) Appl. No.: 13/471,877

(22) Filed: May 15, 2012

(65) Prior Publication Data

US 2012/0302853 A1    Nov. 29, 2012

(30) Foreign Application Priority Data

May 26, 2011    (TW) .............................. 100118524 A (51) Int. Cl.
*A61B 5/00* (2006.01)
*A61B 5/145* (2006.01)
*A61B 5/15* (2006.01)

(52) U.S. Cl.
CPC ........... *A61B 5/6898* (2013.01); *A61B 5/14532* (2013.01); *A61B 5/14546* (2013.01); *A61B 5/150358* (2013.01); *A61B 2560/0443* (2013.01); *A61B 2562/0295* (2013.01)

(58) Field of Classification Search
CPC ............ G01N 33/4905; G01N 33/557; G01N 27/3272; G01N 27/3273; G01N 27/3274; G01N 33/66; G01N 27/28
USPC .................. 422/68.1; 600/301, 345–348, 319
See application file for complete search history.

(56) References Cited

U.S. PATENT DOCUMENTS

| | | | |
|---|---|---|---|
| 6,168,563 B1 * | 1/2001 | Brown | .......................... 600/301 |
| 6,699,188 B2 | 3/2004 | Wessel | |
| 2003/0178322 A1 * | 9/2003 | Iyengar | .............. G01N 27/3274 |
| | | | 205/775 |
| 2010/0249965 A1 | 9/2010 | Rao et al. | |

FOREIGN PATENT DOCUMENTS

CN    101858880 A    10/2010

OTHER PUBLICATIONS

Chinese Office Action dated Sep. 2, 2014, 9 pages.
Search Report from Taiwanese Patent Application No. 101114436 dated Oct. 18, 2014, 1 page.
Office Action from Taiwanese Patent Application No. 101114436 dated Nov. 20, 2014, 6 pages.

* cited by examiner

*Primary Examiner* — Sally Merkling
(74) *Attorney, Agent, or Firm* — Volpe and Koenig, P.C.

(57) ABSTRACT

A measuring method for measuring a physiological parameter via a measuring system comprising a test strip, an auxiliary measuring device and an electronic device having an application program and an analog-to digital converting unit is provided. The measuring method includes steps of coupling the auxiliary measuring device between the test strip and the electronic device to form a loop; the electronic device executing the application program to provide a first analog signal, and transferring the first analog signal to the auxiliary measuring device via the loop; the auxiliary measuring device applying a voltage to the test strip according to the first analog signal, and causing the test strip to generate a second analog signal; the analog-to-digital converting unit converting the second analog signal into a digital signal via the application program; and the application program calculating the digital signal to estimate the physiological parameter.

7 Claims, 9 Drawing Sheets

SYSTEM AND METHOD FOR MEASURING PHYSIOLOGICAL PARAMETERS

CROSS-REFERENCE TO RELATED APPLICATION AND CLAIM OF PRIORITY

The application claims the benefit of Taiwan Patent Application No. 100118524, filed on May 26, 2011, in the Taiwan Intellectual Property Office, the disclosures of which are incorporated herein in their entirety by reference.

FIELD OF THE INVENTION

The present invention relates to a system and method for measuring parameters, and more particularly to a system and method for measuring physiological parameters.

BACKGROUND OF THE INVENTION

Due to changes of the living environment and increase of the aged people, the probability of suffering from hypertension, hyperlipidemin and hyperglycemia is enhanced, and the ages of patients are getting younger and younger. For monitoring body conditions, most people or families have personal health-care devices for measuring blood pressure and blood sugar. However, there are many personal health-care devices with different brands in the market, which have no common standard. Hence, it is time-consuming to integrate the health-care data measured by these personal health-care devices.

Conventionally, an independent measuring device is needed to perform the measurement. The measuring device includes a processor such as a microprocessor control unit (MCU), an analog-to-digital converter (ADC), a storing device such as an electrically erasable programmable read-only memory (EEPROM), a display interface such as an LCD, a general purpose input/output (GPIO), etc., so that it can be operated independently. The measuring device has a more complex hardware structure. Besides, when the measuring device is connected to different electronic devices to perform data integration, different connection interfaces are required, which is very inconvenient.

In order to overcome the drawbacks in the prior art, a system and method for measuring physiological parameters are provided. The particular design in the present invention not only solves the problems described above, but also is easy to be implemented. Thus, the present invention has the utility for the industry.

SUMMARY OF THE INVENTION

In accordance with an aspect of the present invention, a measuring device having a simple hardware structure is provided, which not only reduces the production cost but also enables the user to perform integration with any electronic devices. This greatly enhances the operational convenience for the user.

In accordance with another aspect of the present invention, an auxiliary measuring device is provided. The auxiliary measuring device cooperates with the current electronic device having an application program, uses a common connection interface, e.g. an audio port (for example, a microphone-type audio port) or the 30-pin connection terminal of the I phone, to build the "audio port" connection interface in the electronic device, and measures a test strip including a physiological parameter. Then, the calculation and correction are performed by the application program of the electronic device to obtain the data of the physiological parameter, thereby achieving the effect of measuring physiological parameters. For example, the current electronic device can be a personal computer, a notebook computer, a smart hand-held device, etc.

In accordance with a further aspect of the present invention, a measuring method for measuring a physiological parameter via a measuring system comprising a test strip, an auxiliary measuring device and an electronic device having an application program and an analog-to digital converting unit is provided. The measuring method includes steps of coupling the auxiliary measuring device between the test strip and the electronic device to form a loop; the electronic device executing the application program to provide a first analog signal, and transferring the first analog signal to the auxiliary measuring device via the loop; the auxiliary measuring device applying a voltage to the test strip according to the first analog signal, and causing the test strip to generate a second analog signal; the analog-to-digital converting unit converting the second analog signal into a digital signal via the application program; and the application program calculating the digital signal to estimate the physiological parameter.

In accordance with further another aspect of the present invention, a measuring system for measuring a physiological parameter is provided. The measuring system includes an auxiliary measuring device; an application program; and an analog-to-digital converting unit, wherein the application program indicates the analog-to-digital converting unit to convert an analog signal, which is from the auxiliary measuring device and associated with the physiological parameter, into a digital signal to obtain a measuring datum for the physiological parameter.

Preferably, the measuring system further includes a sensing unit including a test strip sensing the physiological parameter in response to a voltage to generate the analog signal; and the auxiliary measuring device coupled between the test strip and the analog-to-digital converting unit to form a loop, having a power source control unit for supplying the voltage, and sending the analog signal to the analog-to-digital converting unit via the loop.

Preferably, the measuring system further includes an electronic device coupled to the auxiliary measuring device, and including a storing unit storing the digital signal, the application program and a correction datum; a processing unit executing the application program to generate an audio digital signal, calculating the digital signal by using the application program and the correction datum to generate the measuring datum, storing the measuring datum in the storing unit by using the application program, and processing data transmitted from the analog-to-digital converting unit and the storing unit; a display unit displaying the measuring datum for the physiological parameter; the analog-to-digital converting unit; and a digital-to-analog converting unit converting the audio digital signal into an audio analog signal, wherein the audio analog signal is a sensing analog signal having a specific audio frequency.

In accordance with further another aspect of the present invention, a method for measuring a physiological parameter is provided. The method includes steps of providing an electronic device having an analog-to-digital converting unit and an application program; generating an analog signal associated with the physiological parameter; converting the analog signal into a digital signal by using the analog-to-digital converting unit, under an operation of the application program; and measuring the physiological parameter according to the digital signal.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Figure 1:
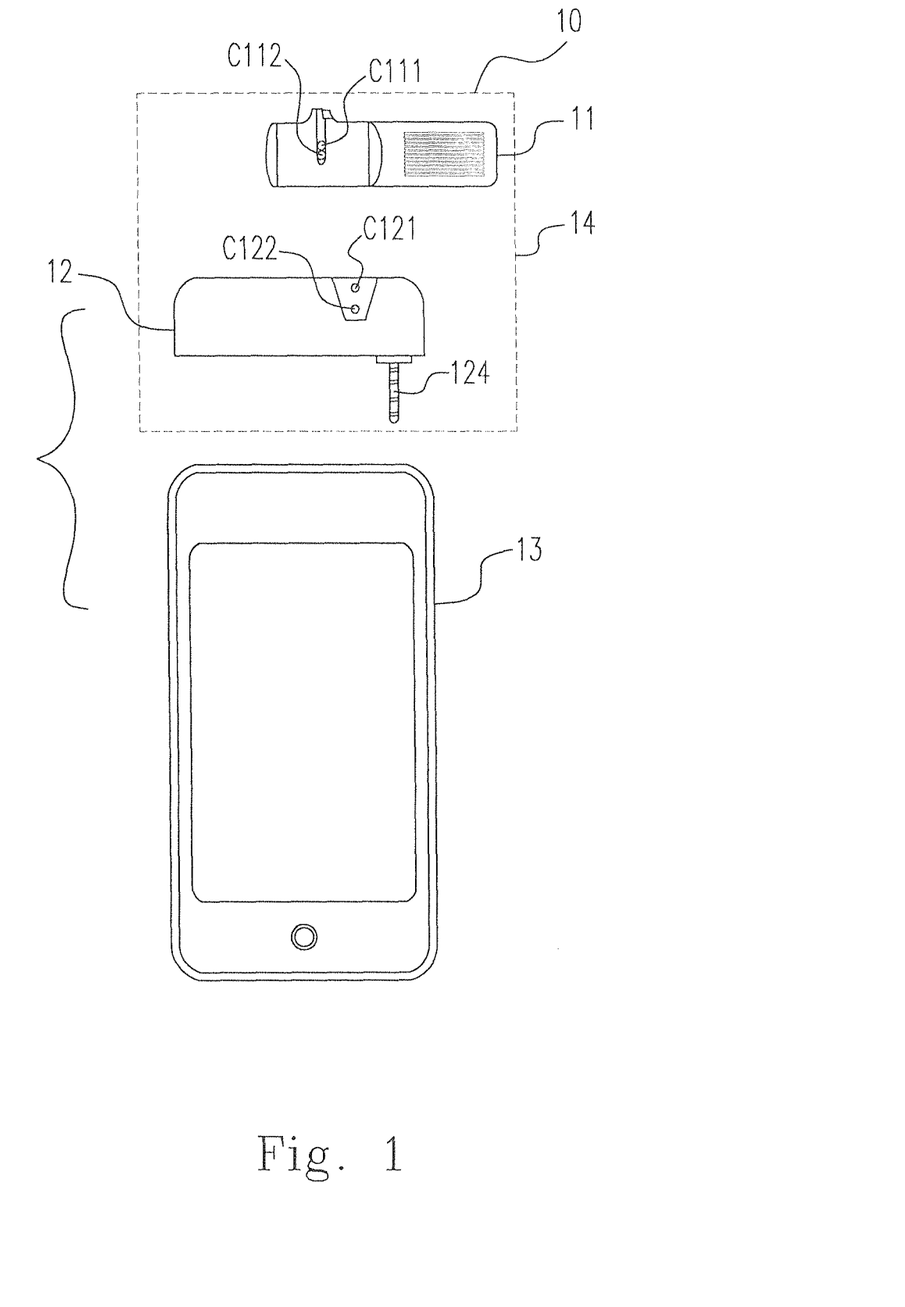
FIG. 1 shows a measuring system according to the present invention.

Please refer to FIG. 1, which shows a measuring system 10 according to the present invention. The measuring system 10 includes an electronic device 13 and a sensing unit 14. The sensing unit 14 includes a test strip 11 and a measuring device 12. The sensing unit 14 can have many types. According to a first type of the sensing unit 14, the test strip 11 and the measuring device 12 are integrated in one device. According to a second type of the sensing unit 14, the test strip 11 is separate from the measuring device 12. The test strip 11 includes two contact points C111, C112. The measuring device 12 includes an audio port plug 124 and at least two contact points C121, C122. The test strip 11 provides various kinds of physiological parameters. For example, the physiological parameter includes at least one of physiological parameters associated with the blood sugar concentration and the cholesterol concentration. The two contact points C111, C112 of the test strip 11 are coupled to the two contact points C121, C122 of the measuring device 12 respectively. The measuring device 12 is coupled to the electronic device 13 via the audio port plug 124. For example, the electronic device 13 can be a smart hand-held device, a notebook computer or a personal computer.

Figure 2:
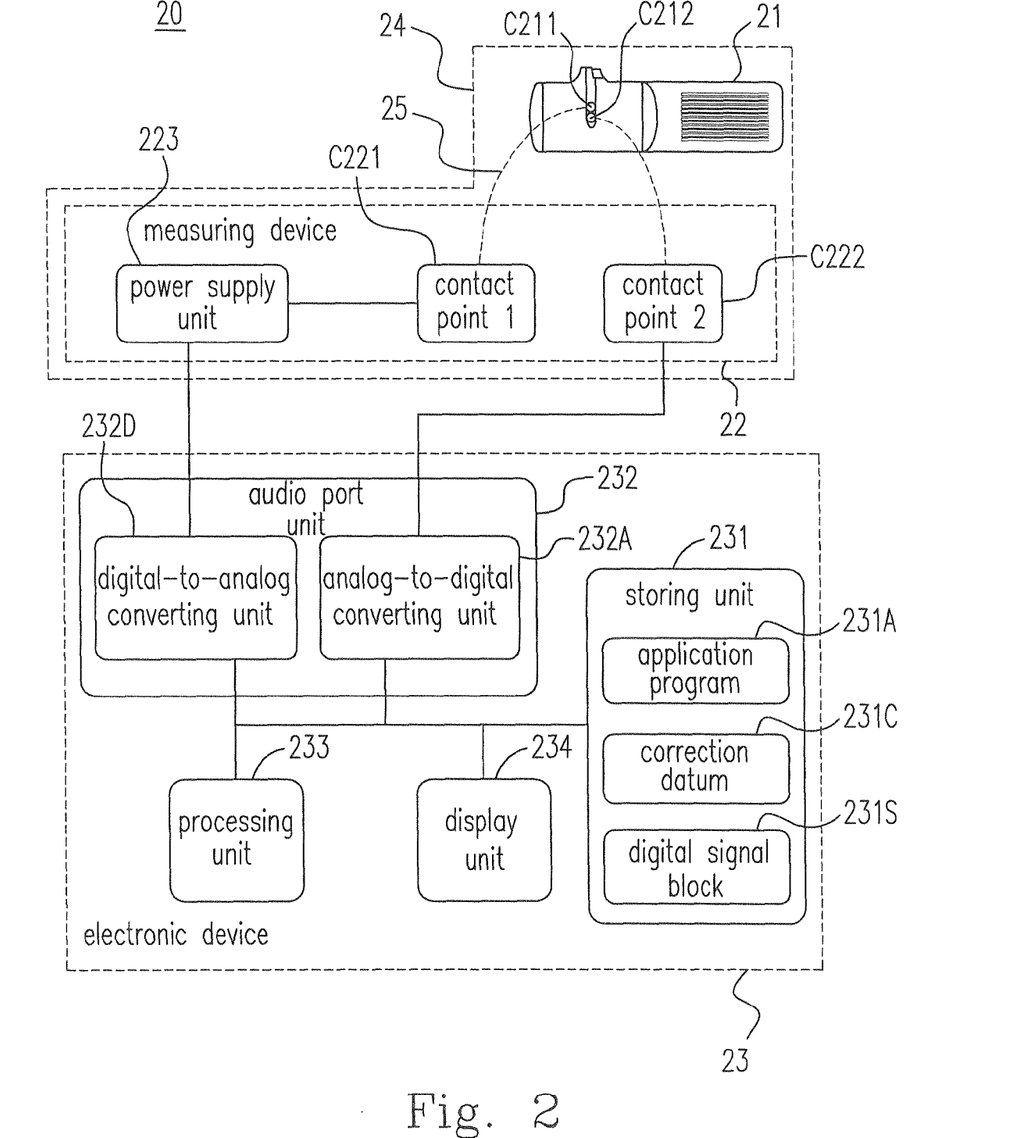
FIG. 2 shows the structure of a measuring system according to a first embodiment of the present invention.

Please refer to FIG. 2, which shows the structure of a measuring system 20 according to a first embodiment of the present invention. The measuring system 20 includes an electronic device 23 and a sensing unit 24. The sensing unit 24 includes a test strip 21 and a measuring device 22. The sensing unit 24 can be variety of types. According to a first type of the sensing unit 24, the test strip 21 and the measuring device 22 are integrated in one device. According to a second type of the sensing unit 24, the test strip 21 is separate from the measuring device 22. The test strip 21 includes two contact points C211, C212. The measuring device 22 includes a power source control unit 223 and at least two contact points C221, C222. The electronic device 23 includes a storing unit 231, an audio port unit 232, a processing unit 233 and a display unit 234. The audio port unit 232 includes an analog-to-digital converting unit 232A and a digital-to-analog converting unit 232D. The storing unit 231 includes a digital signal block 231S, an application program 231A and a correction datum 231C.

The contact points C211, C212 of the test strip 21 are coupled to the contact points C221, C222 of the measuring device 22 respectively to form a loop 25. The test strip 21 senses a physiological parameter in response to a voltage to generate an analog signal. The measuring device 22 is coupled between the test strip 21 and the audio port unit 232 for providing the voltage, and transferring the analog signal to the audio port unit 232. For example, the analog signal is a feedback analog signal associated with the physiological parameter, and the feedback analog signal is a current-dependent analog signal or a voltage-dependent analog signal.

When the measuring device 22 receives power from the electronic device 23, the power source control unit 223 is a signal converting unit for converting a first audio analog signal into the voltage.

The audio port unit 232 converts the feedback analog signal associated with the physiological parameter into a digital signal, so as to measure the physiological parameter. For example, the digital signal is a final digital signal. The analog-to-digital converting unit 232A of the audio port unit 232 converts the feedback analog signal into the final digital signal. For example, the feedback analog signal is an analog signal indicating the variation degree of the voltage or current, and the final digital signal is a digital signal indicating the variation degree of the voltage or current. The digital-to-analog converting unit 232D converts the original digital signal into the sensing analog signal. For example, the original digital signal is an audio digital signal, and the sensing analog signal is an audio analog signal.

The storing unit 231 stores the digital signal block 231S, the application program 231A and the correction datum 231C. The digital signal block 231S stores the collected final digital signal. The processing unit 233 processes the digital signal block 231S by using the application program 231A and the correction datum 231C, so as to generate a measuring datum, stores the measuring datum in the storing unit 231 by using the application program 231A, and processes data transmitted from the analog-to-digital converting unit 232A and the storing unit 231. The measuring datum includes a quantitative physiological parameter for indicating the physiological parameter. The display unit 234 displays the measuring datum for the physiological parameter. The physiological parameter includes at least one of physiological parameters associated with the blood sugar concentration and the cholesterol concentration.

Figure 3:
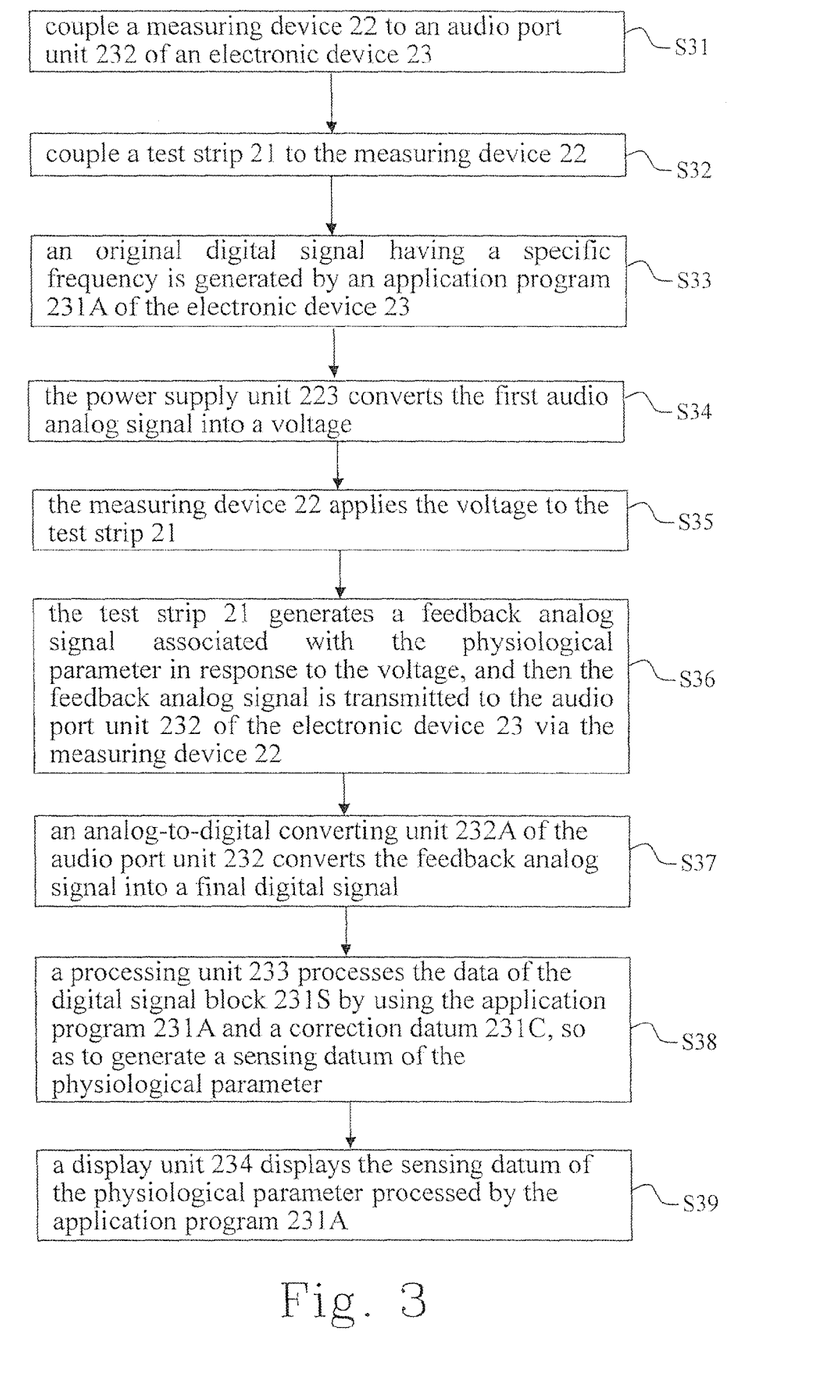
FIG. 3 is a flowchart of a measuring method for the measuring system according to the first embodiment of the present invention.

Please refer to FIG. 3, which is a flowchart of a measuring method for the measuring system 20 according to the first embodiment of the present invention. In the step S31, a measuring device 22 is coupled to an audio port unit 232 of an electronic device 23. In the step S32, a test strip 21 is coupled to the measuring device 22 to form a loop 25. In the step S33, an original digital signal having a specific frequency is generated by an application program 231A of the electronic device 23. For example, the original digital signal is an audio digital signal. The original digital signal is converted into a first audio analog signal by a digital-to-analog converting unit 232D of the audio port unit 232, and then the digital-to-analog converting unit 232D transfers the first audio analog signal to the measuring device 22. In the step S34, when the measuring device 22 receives power from the electronic device 23, a power source control unit 223 in the measuring device 22 is a signal converting unit, and the power source control unit 223 converts the first audio analog signal into a voltage. In the step S35, the measuring device 22 applies the voltage to the test strip 21. In the step S36, the test strip 21 generates a feedback analog signal associated with the physiological parameter in response to the voltage. For example, the feedback analog signal is a current-dependent analog signal or a voltage-dependent analog signal. The feedback analog signal is transmitted to the audio port unit 232 of the electronic device 23 via the measuring device 22. In the step S37, an analog-to-digital converting unit 232A of the audio port unit 232 converts the feedback analog signal into a final digital signal, and stores the final digital signal in a digital signal block 231S. In the step S38, a processing unit 233 processes the data of the digital signal block 231S by using the application program 231A and a correction datum 231C, so as to generate a measuring datum. The measuring datum includes a quantitative physiological parameter for indicating the physiological parameter. In the step S39, a display unit 234 displays the measuring datum for the physiological parameter processed by the application program 231A. In the embodiments of the present invention, the physiological parameter includes at least one of physiological parameters associated with the blood sugar concentration and the cholesterol concentration.

Figure 4:
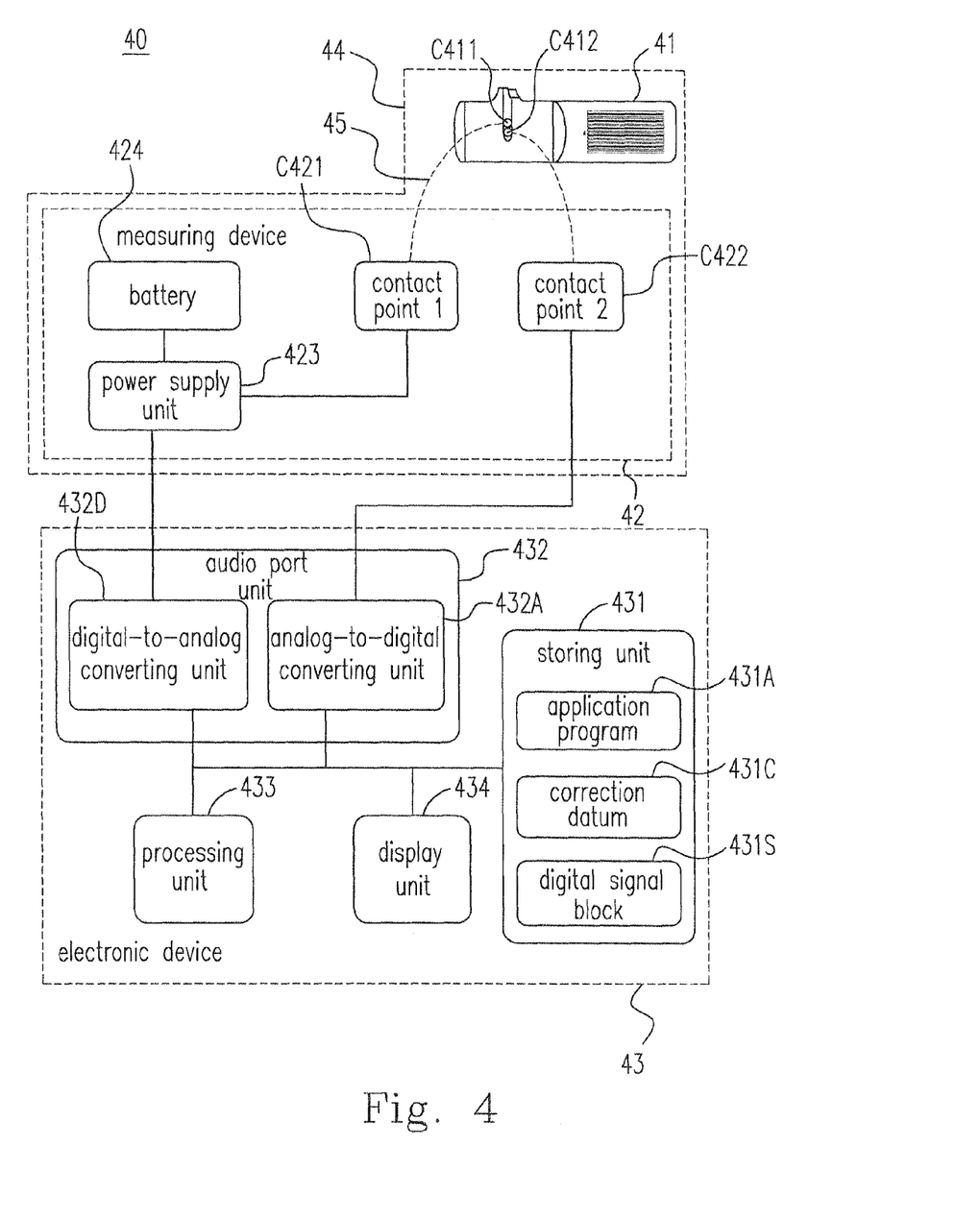
FIG. 4 shows the structure of a measuring system according to a second embodiment of the present invention.

Please refer to FIG. 4, which shows the structure of a measuring system 40 according to a second embodiment of the present invention. The measuring system 40 includes an electronic device 43 and a sensing unit 44. The sensing unit 44 includes a test strip 41 and a measuring device 42. The sensing unit 44 can have many types. According to a first type of the sensing unit 44, the test strip 41 and the measuring device 42 are integrated in one device. According to a second type of the sensing unit 44, the test strip 41 is separate from the measuring device 42. The test strip 41 includes two contact points C411, C412. The measuring device 42 includes a power source control unit 423, a battery 424 and at least two contact points C421, C422. The electronic device 43 includes a storing unit 431, an audio port unit 432, a processing unit 433 and a display unit 434. The audio port unit 432 includes an analog-to-digital converting unit 432A and a digital-to-analog converting unit 432D. The storing unit 431 includes a digital signal block 431S, an application program 431A and a correction datum 431C.

The contact points C411, C412 of the test strip 41 are coupled to the contact points C421, C422 of the measuring device 42 respectively to form a loop 45. The test strip 41 senses a physiological parameter in response to a voltage to generate an analog signal. The measuring device 42 is coupled between the test strip 41 and the audio port unit 432, provides the voltage, and transfers the analog signal to the audio port unit 432. For example, the analog signal is a feedback analog signal associated with the physiological parameter, and the feedback analog signal is a current-dependent analog signal or a voltage-dependent analog signal.

When the measuring device 42 includes the battery 424, the power source control unit 423 is a switch control unit for switching a first voltage mode to a second voltage mode in response to a second audio analog signal to cause the battery 424 to provide the voltage.

The audio port unit 432 converts the feedback analog signal associated with the physiological parameter into a digital signal to measure the physiological parameter. For example, the digital signal is a final digital signal. The analog-to-digital converting unit 432A of the audio port unit 432 converts the feedback analog signal into the final digital signal. For example, the feedback analog signal is an analog signal indicating the variation degree of the voltage or current, and the final digital signal is a digital signal indicating the variation degree of the voltage or current. The digital-to-analog converting unit 432D converts the original digital signal into the sensing analog signal. For example, the original digital signal is an audio digital signal, and the sensing analog signal is an audio analog signal.

The storing unit 431 stores the digital signal block 431S, the application program 431A and the correction datum 431C. The digital signal block 431S stores the collected final digital signal. The processing unit 433 processes the digital signal block 431S by using the application program 431A and the correction datum 431C to generate a measuring datum, stores the measuring datum in the storing unit 431 by using the application program 431A, and processes data sent by the analog-to-digital converting unit 432A and the storing unit 431. The measuring datum includes a quantitative physiological parameter for indicating the physiological parameter. The display unit 434 displays the measuring datum for the physiological parameter. In the embodiments of the present invention, the physiological parameter includes at least one of physiological parameters associated with the blood sugar concentration and the cholesterol concentration.

Figure 5:
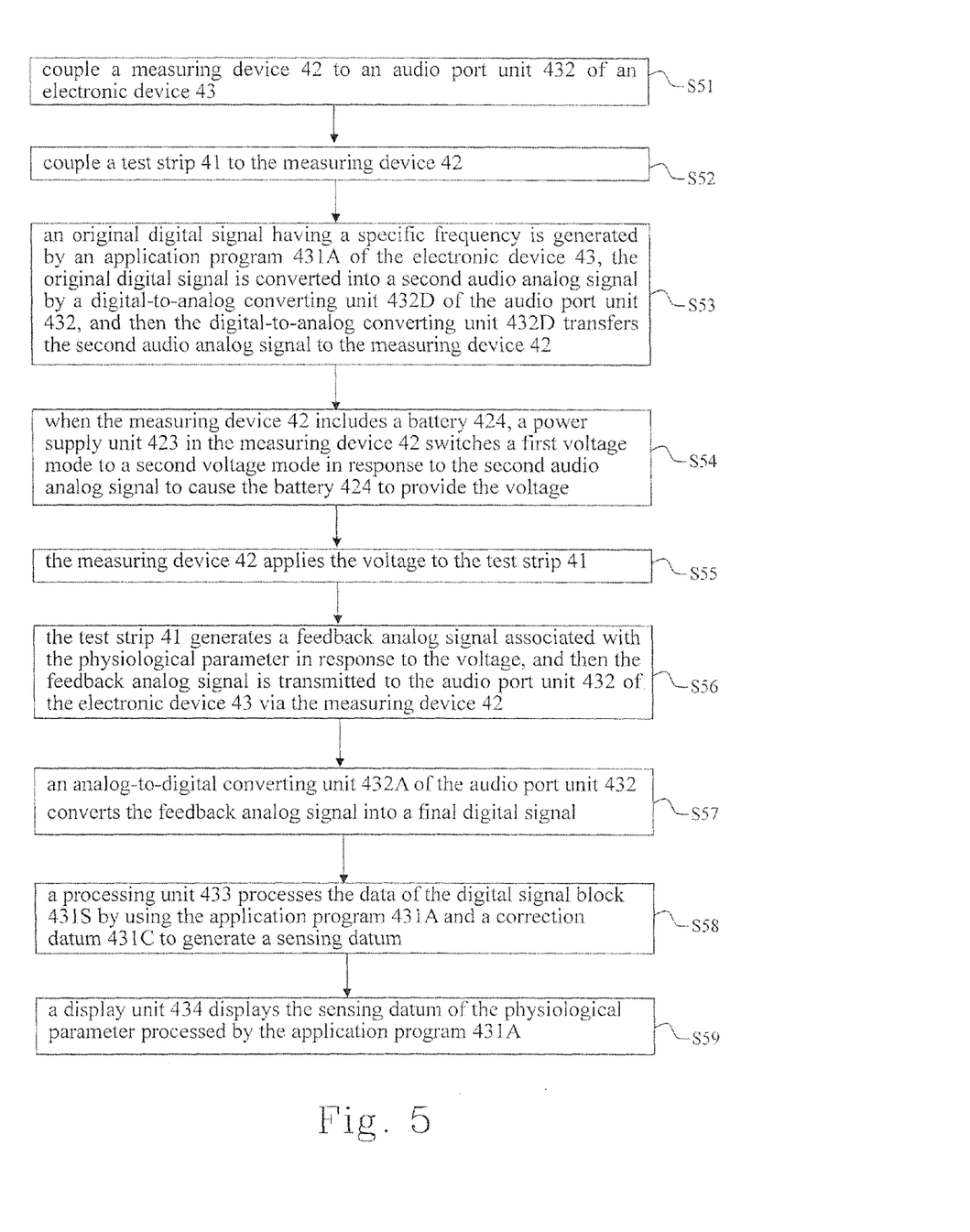
FIG. 5 is a flowchart of a measuring method for the measuring system according to the second embodiment of the present invention.

Please refer to FIG. 5, which is a flowchart of a measuring method for the measuring system 40 according to the second embodiment of the present invention. In the step S51, a measuring device 42 is coupled to an audio port unit 432 of an electronic device 43. In the step S52, a test strip 41 is coupled to the measuring device 42 to form a loop 45. In the step S53, an original digital signal having a specific frequency is generated by an application program 431A of the electronic device 43. For example, the original digital signal is an audio digital signal. The original digital signal is converted into a second audio analog signal by a digital-to-analog converting unit 432D of the audio port unit 432, and then the digital-to-analog converting unit 432D transfers the second audio analog signal to the measuring device 42. In the step S54, when the measuring device 42 includes a battery 424, a power source control unit 423 in the measuring device 42 is a switch control unit for switching a first voltage mode to a second voltage mode in response to the second audio analog signal to cause the battery 424 to provide the voltage. In the step S55, the measuring device 42 applies the voltage to the test strip 41. In the step S56, the test strip 41 generates a feedback analog signal associated with the physiological parameter in response to the voltage. For example, the feedback analog signal is a current-dependent analog signal or a voltage-dependent analog signal. The feedback analog signal is transmitted to the audio port unit 432 of the electronic device 43 via the measuring device 42. In the step S57, an analog-to-digital converting unit 432A of the audio port unit 432 converts the feedback analog signal into a final digital signal, and stores the final digital signal in a digital signal block 431S. In the step S58, a processing unit 433 processes the data of the digital signal block 431S by using the application program 431A and a correction datum 431C to generate a measuring datum. The measuring datum includes a quantitative physiological parameter for indicating the physiological parameter. In the step S59, a display unit 434 displays the measuring datum for the physiological parameter processed by the application program 431A. In the embodiments of the present invention, the physiological parameter includes at least one of physiological parameters associated with the blood sugar concentration and the cholesterol concentration.

Figure 6:
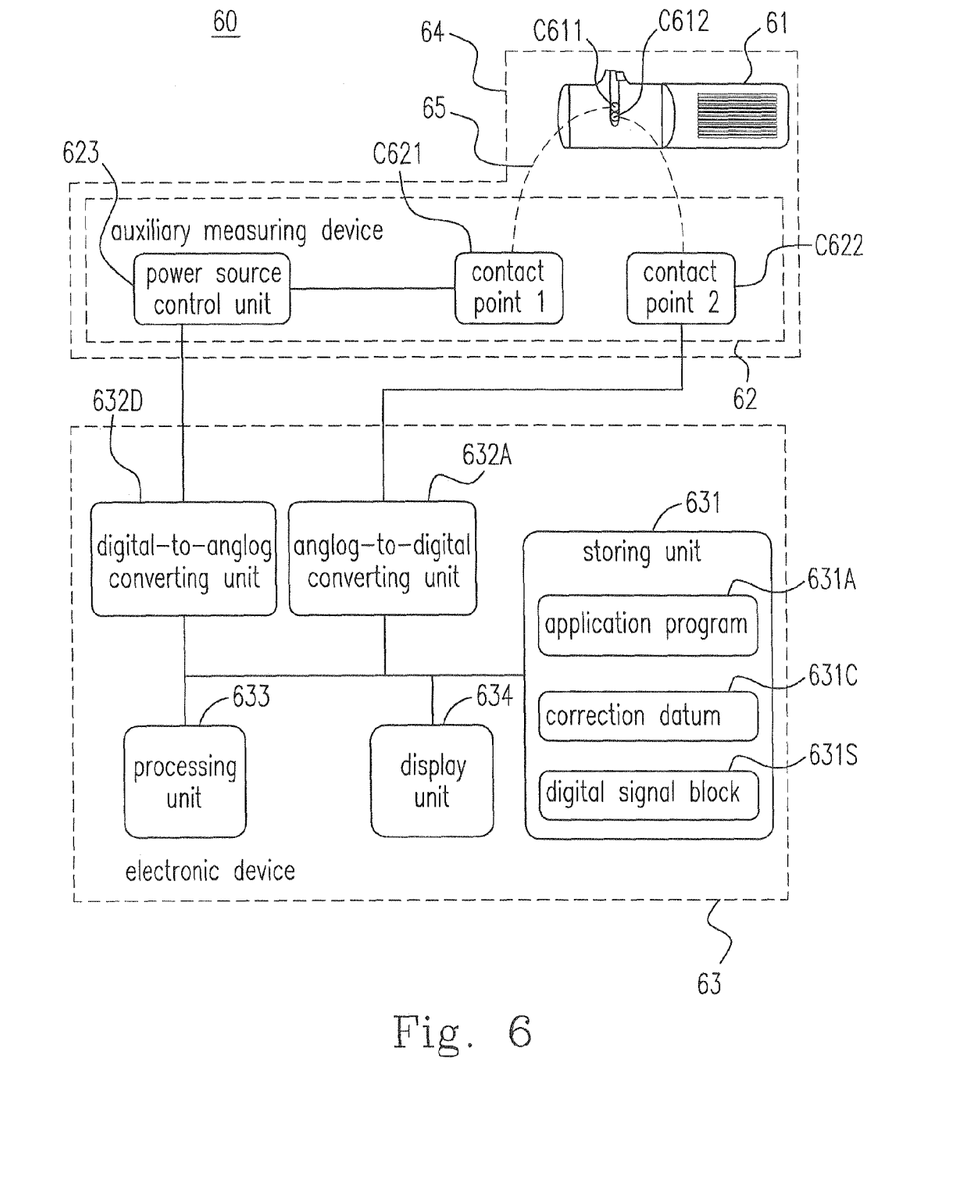
FIG. 6 shows the structure of a measuring system according to a third embodiment of the present invention.

Please refer to FIG. 6, which shows the structure of a measuring system 60 according to a third embodiment of the present invention. The measuring system 60 includes an electronic device 63 and a sensing unit 64. The sensing unit 64 includes a test strip 61 and an auxiliary measuring device 62. The sensing unit 64 can be variety of types. The electronic device can be a computer or a smart mobile device, e.g. the cellphone, PDA or iPAD. According to a first type of the sensing unit 64, the test strip 61 and the auxiliary measuring device 62 are integrated in one device. According to a second type of the sensing unit 64, the test strip 61 is separate from the measuring device 62. The test strip 61 includes two contact points C611, C612. The auxiliary measuring device 62 includes a power source control unit 623 and at least two contact points C621, C622. The electronic device 63 includes a storing unit 631, an analog-to-digital converting unit 632A, a digital-to-analog converting unit 632D, a processing unit 633 and a display unit 634. The storing unit 231 includes a digital signal block 631S, an application program 631A and a correction datum 631C. Usually, the application program 631A is an APP program for the computer or the smart mobile device, e.g. the iOS software, Android, Windows Mobil Phone App software, etc.

The processing unit 633 executes the application program 631A to generate an audio digital signal, and converts the audio digital signal into an audio analog signal by using the digital-to-analog converting unit 632D. In one embodiment, the audio analog signal is an audio voltage signal. As shown in FIG. 6, the contact points C611, C612 of the test strip 61 are coupled to the contact points C621, C622 of the auxiliary measuring device 62 respectively to form a loop 65. The test strip 61 senses a physiological parameter in response to a voltage to generate an analog signal. In one embodiment, the power source control unit 623 generates the voltage according to the audio analog signal; in another embodiment, the audio voltage signal directly provides the voltage. The auxiliary measuring device 62 is coupled between the test strip 61 and the electronic device 63, and transfers the analog signal to the electronic device 63. For example, the analog signal is a feedback analog signal associated with the physiological parameter, and the feedback analog signal is a current-dependent analog signal or a voltage-dependent analog signal.

The electronic device 63 can supply the power required for the auxiliary measuring device 62. When the auxiliary measuring device 62 receives power from the electronic device 63, the power source control unit 623 is a signal converting unit for converting the audio analog signal into the voltage.

The analog-to-digital converting unit 632A converts the analog signal into a digital signal according to the command sent by the application program 631A, so as to obtain the measuring datum for the physiological parameter in the subsequent operation. For example, the digital signal is a final digital signal. The analog-to-digital converting unit 632A converts the feedback analog signal into the final digital signal. For example, the feedback analog signal is an analog signal indicating the variation degree of the voltage or current, and the final digital signal is a digital signal indicating the variation degree of the voltage or current. The digital-to-analog converting unit 632D converts the original digital signal into the sensing analog signal. For example, the original digital signal is an audio digital signal, and the sensing analog signal is an audio analog signal.

The storing unit 631 stores the digital signal block 631S, the application program 631A and the correction datum 631C. The digital signal block 631S stores the collected final digital signal. The processing unit 633 processes the digital signal block 631S by using the application program 631A and the correction datum 631C so as to generate a measuring datum, stores the measuring datum in the storing unit 631 by using the application program 631A, and processes data transmitted from the analog-to-digital converting unit 632A and the storing unit 631. The measuring datum includes a quantitative physiological parameter for indicating the physiological parameter. The display unit 634 displays the measuring datum for the physiological parameter. The physiological parameter includes at least one of physiological parameters associated with the blood sugar concentration and the cholesterol concentration.

Figure 7:
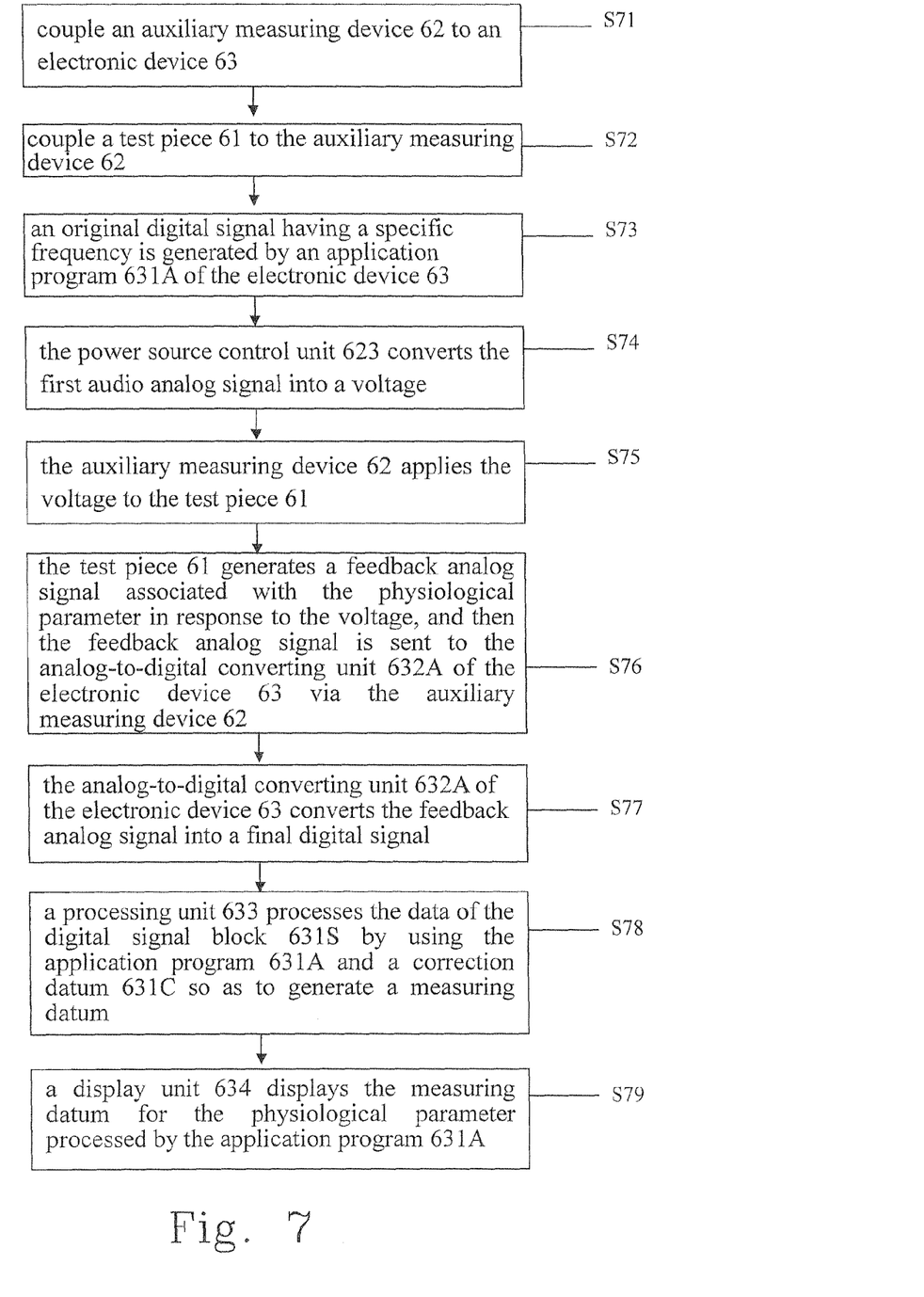
FIG. 7 is a flowchart of a measuring method for the measuring system according to the third embodiment of the present invention.

Please refer to FIG. 7, which is a flowchart of a measuring method for the measuring system 60 according to the third embodiment of the present invention. In the step S71, an auxiliary measuring device 62 is coupled to an electronic device 63. In the step S72, a test strip 61 is coupled to the auxiliary measuring device 62 to form a loop 65. In the step S73, an original digital signal having a specific frequency is generated by an application program 631A of the electronic device 63. For example, the original digital signal is an audio digital signal. The original digital signal is converted into a first audio analog signal by a digital-to-analog converting unit 632D of the electronic device 63, and then the digital-to-analog converting unit 632D transfers the first audio analog signal to the auxiliary measuring device 62. In the step S74, when the auxiliary measuring device 62 receives power from the electronic device 63, a power source control unit 623 in the measuring device 62 is a signal converting unit, and the power source control unit 623 converts the first audio analog signal into a voltage. In the step S75, the auxiliary measuring device 62 applies the voltage to the test strip 61. In the step S76, the test strip 61 generates a feedback analog signal associated with the physiological parameter in response to the voltage. For example, the feedback analog signal is a current-dependent analog signal or a voltage-dependent analog signal. The feedback analog signal is transmitted to an analog-to-digital converting unit 632A of the electronic device 63 via the auxiliary measuring device 62. In the step S77, the analog-to-digital converting unit 632A of the electronic device 63 converts the feedback analog signal into a final digital signal, and stores the final digital signal in a digital signal block 631S. In the step S78, a processing unit 633 processes the data of the digital signal block 631S by using the application program 631A and a correction datum 631C so as to generate a measuring datum. The measuring datum includes a quantitative physiological parameter for indicating the physiological parameter. In the step S79, a display unit 634 displays the measuring datum for the physiological parameter processed by the application program 631A. In the embodiments of the present invention, the physiological parameter includes at least one of physiological parameters associated with the blood sugar concentration and the cholesterol concentration.

Figure 8:
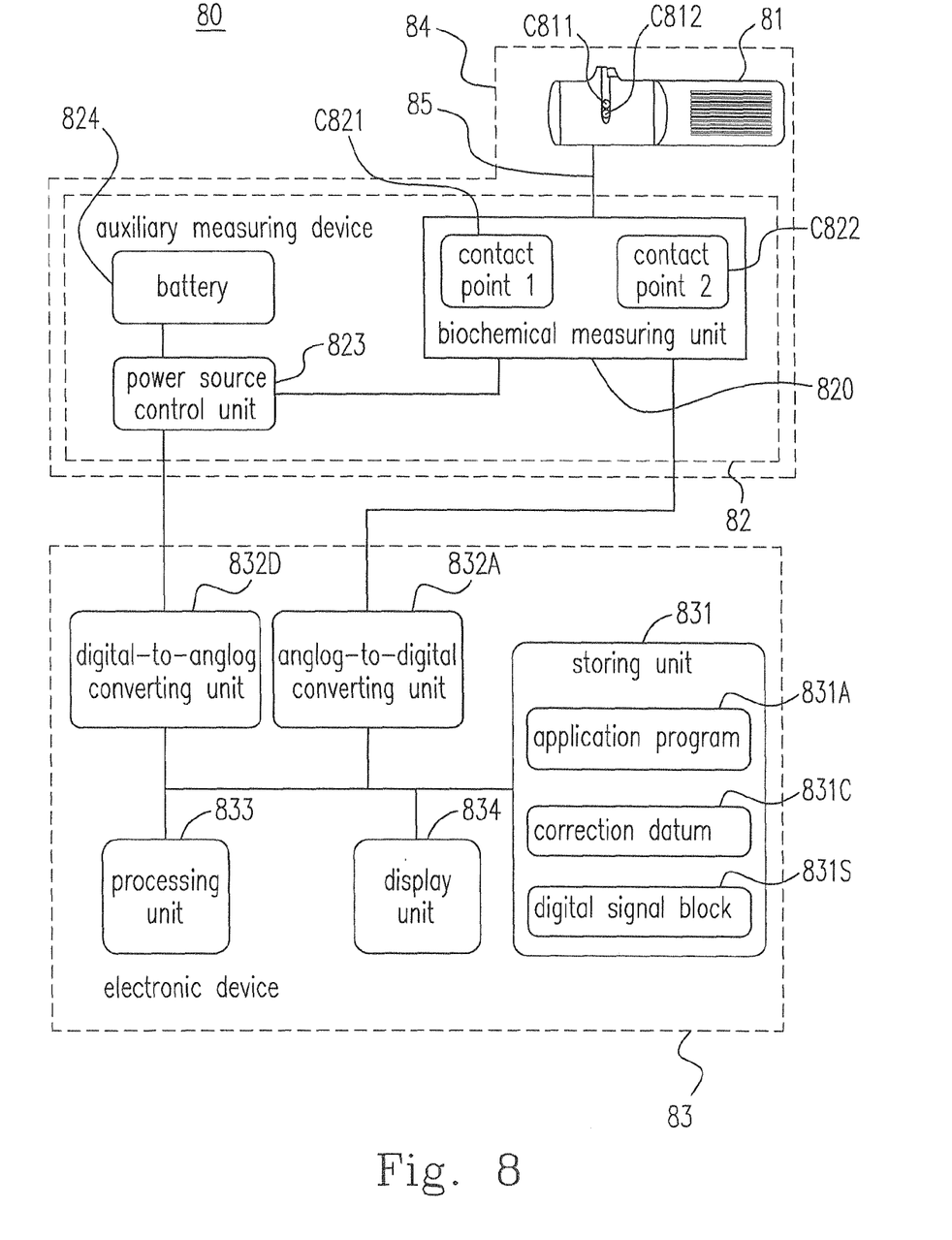
FIG. 8 shows the structure of a measuring system according to a fourth embodiment of the present invention.

Please refer to FIG. 8, which shows the structure of a measuring system 80 according to a fourth embodiment of the present invention. The measuring system 80 includes an electronic device 83 and a sensing unit 84. The sensing unit 84 includes a test strip 81 and an auxiliary measuring device 82. The sensing unit 84 can be variety of types. According to a first type of the sensing unit 84, the test strip 81 and the auxiliary measuring device 82 are integrated in one device. According to a second type of the sensing unit 84, the test strip 81 is separate from the measuring device 82. The test strip 81 includes two contact points C811, C812. The auxiliary measuring device 82 includes a power source control unit 823, a battery 824 and at least two contact points C821, C822. The electronic device 83 includes a storing unit 831, an analog-to-digital converting unit 832A, a digital-to-analog converting unit 832D, a processing unit 833 and a display unit 834. The storing unit 831 includes a digital signal block 831S, an application program 831A and a correction datum 831C. Usually, the application program 831A is an APP program for the computer or the smart mobile device, e.g. the iOS software, Android, Windows Mobil Phone App software, etc.

As shown in FIG. 8, an original digital signal having a specific frequency is generated by an application program 831A of the electronic device 83. For example, the original digital signal is an audio digital signal. The original digital signal is converted into a first audio analog signal by a digital-to-analog converting unit 832D of the electronic device 83, and then the digital-to-analog converting unit 832D transfers the first audio analog signal to the auxiliary measuring device 82. The auxiliary measuring device 82 includes the power source control unit 823 and a biochemical measuring unit 820. When the auxiliary measuring device 82 includes the battery 824, the power source control unit 823 is a switch control unit for switching a first voltage mode to a second voltage mode in response to a second audio analog signal to cause the battery 824 to provide the voltage.

The contact points C811, C812 of the test strip 81 are coupled to the contact points C821, C822 in the biochemical measuring unit 820 respectively to form a loop 85. The test strip 81 senses a physiological parameter in response to a voltage to generate an analog signal. The auxiliary measuring device 82 is coupled between the test strip 81 and the electronic device 83, provides the voltage, and transfers the analog signal to the analog-to-digital converting unit 832A. For example, the analog signal is a feedback analog signal associated with the physiological parameter, and the feedback analog signal is a current-dependent analog signal or a voltage-dependent analog signal.

The analog-to-digital converting unit 832A converts the analog signal into a digital signal according to the command sent by the application program 831A, so as to obtain the measuring datum for the physiological parameter in the subsequent operation. For example, the digital signal is a final digital signal. The analog-to-digital converting unit 832A converts the feedback analog signal into the final digital signal. For example, the feedback analog signal is an analog signal indicating the variation degree of the voltage or current, and the final digital signal is a digital signal indicating the variation degree of the voltage or current.

The storing unit 831 stores the digital signal block 831S, the application program 831A and the correction datum 831C. The digital signal block 831S stores the final digital signal. The processing unit 833 processes the digital signal block 831S by using the application program 831A and the correction datum 831C so as to generate a measuring datum, stores the measuring datum in the storing unit 831 by using the application program 831A, and processes data transmitted from the analog-to-digital converting unit 832A and the storing unit 831. The measuring datum includes a quantitative physiological parameter for indicating the physiological parameter. The display unit 834 displays the measuring datum for the physiological parameter. The physiological parameter includes at least one of physiological parameters associated with the blood sugar concentration and the cholesterol concentration.

Figure 9:
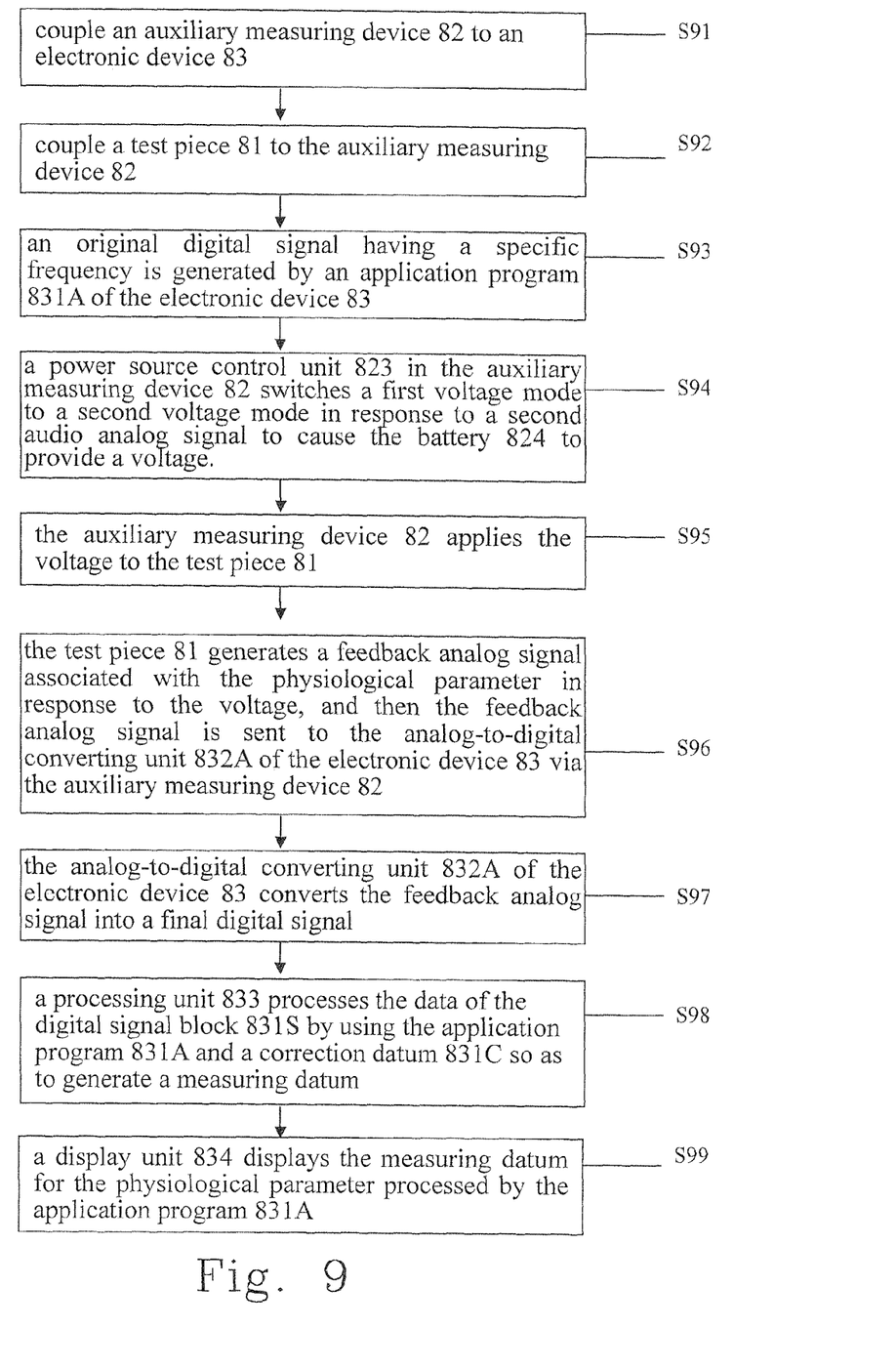
FIG. 9 is a flowchart of a measuring method for the measuring system according to the fourth embodiment of the present invention.

Please refer to FIG. 9, which is a flowchart of a measuring method for the measuring system 80 according to the fourth embodiment of the present invention. In the step S91, an auxiliary measuring device 82 is coupled to an electronic device 83. In the step S92, a test strip 81 is coupled to the auxiliary measuring device 82 to form a loop 85. In the step S93, an original digital signal having a specific frequency is generated by an application program 831A of the electronic device 83. For example, the original digital signal is an audio digital signal. The original digital signal is converted into a first audio analog signal by a digital-to-analog converting unit 832D of the electronic device 83, and then the digital-to-analog converting unit 832D transfers the first audio analog signal to the auxiliary measuring device 82. In the step S94, when the auxiliary measuring device 82 includes a battery 824, a power source control unit 823 in the auxiliary measuring device 82 is a switch control unit for switching a first voltage mode to a second voltage mode in response to a second audio analog signal to cause the battery 824 to provide a voltage. In the step S95, the auxiliary measuring device 82 applies the voltage to the test strip 81. In the step S96, the test strip 81 generates a feedback analog signal associated with the physiological parameter in response to the voltage. For example, the feedback analog signal is a current-dependent analog signal or a voltage-dependent analog signal. The feedback analog signal is transmitted to an analog-to-digital converting unit 832A of the electronic device 83 via the auxiliary measuring device 82. In the step S97, the analog-to-digital converting unit 832A of the electronic device 83 converts the feedback analog signal into a final digital signal, and stores the final digital signal in a digital signal block 831S. In the step S98, a processing unit 833 processes the data of the digital signal block 831S by using the application program 831A and a correction datum 831C so as to generate a measuring datum. The measuring datum includes a quantitative physiological parameter for indicating the physiological parameter. In the step S99, a display unit 834 displays the measuring datum for the physiological parameter processed by the application program 831A. In the embodiments of the present invention, the physiological parameter includes at least one of physiological parameters associated with the blood sugar concentration and the cholesterol concentration.

The present invention only needs to cooperate with a test strip suitable for different physiological parameters, and connect to an electronic device via an auxiliary measuring device. The electronic device can obtain the signal generated by the auxiliary measuring device via a specific application program so that the electronic device can perform the measuring operation. Accordingly, when a general electronic device can cooperate with a suitable APP to provide the inspecting function, the method and device for measuring the physiological parameter of the present invention does not need to use the physiological inspecting device having an inspecting capability. Therefore, the present invention can save the configuration of the processing unit, the storing unit and the display unit, thereby greatly reducing the production cost. On the other hand, the auxiliary measuring device can perform the measuring operation by connecting an audio port or a USB connector to an electronic device, and installing a specific application program in the electronic device. For example, the electronic device is a computer or a smart mobile device. Hence, the present invention simplifies the method and device for measuring the physiological parameter. To compare with the prior art, the present invention uses the audio port (such as a microphone-type audio port) which can be built in each electronic device collectively and be used commonly. This greatly overcomes the inconvenience resulting from different connection interfaces of different devices.

Power Source Control Unitpower Source Control Unitpower Source Control Unit

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A measuring method for measuring a physiological parameter via a measuring system comprising a test strip, an auxiliary measuring device and an electronic device having an application program, a correction datum, digital-to-analog converting (DAC) unit and an analog-to digital converting (ADC) unit, comprising steps of:
   coupling the auxiliary measuring device to the electronic device through an audio port, and the auxiliary measuring device forms a loop between the test strip and the electronic device;
   the electronic device executing the application program to initialize a measuring procedure by generating a first digital signal, wherein said first digital signal is an audio digital signal with a specific frequency;
   the DAC unit converting the first digital signal to a first analog signal, and transferring the first analog signal to the auxiliary measuring device via the loop;
   the auxiliary measuring device applying a voltage to the test strip according to the first analog signal, and causing the test strip to generate a second analog signal;
   the ADC unit converting the second analog signal into a second digital signal via the application program; and
   the correction datum and the application program are used to correct and calculate the second digital signal to estimate the physiological parameter.

2. A method as claimed in claim 1, wherein when the auxiliary measuring device receives a power from the electronic device, the auxiliary measuring device converts the first analog signal into the voltage.

3. A method as claimed in claim 1, wherein when the auxiliary measuring device includes a battery, the auxiliary measuring device switches a first voltage mode to a second voltage mode in response to a third analog signal to cause the battery to provide the voltage.

4. A method as claimed in claim 1, wherein the physiological parameter comprises at least one of physiological parameters associated with a blood sugar concentration and a cholesterol concentration.

5. A method as claimed in claim 1, wherein the first analog signal is an audio signal.

6. A method for measuring a physiological parameter, comprising steps of:
   providing an electronic device having an analog-to-digital converting (ADC) unit, a digital-to-analog converting (DAC) unit, and an application program and a correction datum;
   generating a first digital signal having a specific frequency by the application program to initialize a measuring procedure, wherein the first digital signal is an audio digital signal;
   converting the first digital signal to a first analog signal by the DAC unit, wherein the first analog signal is an audio analog signal;
   transferring the first analog signal to an auxiliary measuring device through an audio port;
   converting the first analog signal into a voltage by a power source control unit;
   generating a second analog signal associated with the physiological parameter based on the voltage;
   transferring the second analog signal to the electronic device through the audio port;
   converting the second analog signal into a second digital signal by using the ADC unit, under an operation of the application program; and
   correcting and measuring the physiological parameter by using the correction datum and the application program according to the second digital signal.

7. A method as claimed in claim 6, wherein the physiological parameter comprises at least one of physiological parameters associated with a blood sugar concentration and a cholesterol concentration.

* * * * *